(12) United States Patent
Wu et al.

(10) Patent No.: US 8,446,586 B2
(45) Date of Patent: May 21, 2013

(54) METHOD AND APPARATUS FOR INCREASING ADIPOSE VASCULAR FRACTION

(76) Inventors: Allan Yang Wu, Cathedral City, CA (US); David Martin Morrow, Rancho Mirage, CA (US)

( * ) Notice: Subject to any disclaimer, the term of this patent is extended or adjusted under 35 U.S.C. 154(b) by 470 days.

(21) Appl. No.: 12/578,549

(22) Filed: Oct. 13, 2009

(65) Prior Publication Data
US 2010/0112084 A1 May 6, 2010

Related U.S. Application Data

(60) Provisional application No. 61/136,931, filed on Oct. 15, 2008.

(51) Int. Cl.
*G01N 21/00* (2006.01)
*G01J 5/02* (2006.01)
*A61B 5/00* (2006.01)
*A61B 6/00* (2006.01)

(52) U.S. Cl.
USPC ............ 356/432; 250/339.01; 250/339.05; 250/339.11; 250/339.12; 250/343; 422/82.05; 422/82.09; 436/164; 600/310; 600/322; 600/328; 600/473; 600/476

(58) Field of Classification Search
None
See application file for complete search history.

(56) References Cited

U.S. PATENT DOCUMENTS

| | | | | |
|---|---|---|---|---|
| 4,558,947 A | * | 12/1985 | Wardlaw | 356/39 |
| 5,002,538 A | * | 3/1991 | Johnson | 604/240 |
| 5,012,845 A | * | 5/1991 | Averette | 141/329 |
| 5,525,240 A | * | 6/1996 | Lemelson | 210/745 |
| 5,857,462 A | * | 1/1999 | Thomas et al. | 600/310 |
| 5,888,184 A | * | 3/1999 | Wardlaw | 494/37 |
| 6,020,196 A | * | 2/2000 | Hu et al. | 435/366 |
| 6,391,297 B1 | * | 5/2002 | Halvorsen | 424/93.7 |
| 6,512,936 B1 | * | 1/2003 | Monfre et al. | 600/322 |
| 6,587,702 B1 | * | 7/2003 | Ruchti et al. | 600/310 |
| 7,761,139 B2 | * | 7/2010 | Tearney et al. | 600/473 |
| 7,922,688 B2 | * | 4/2011 | Bodduluri et al. | 604/62 |
| 2005/0123895 A1 | * | 6/2005 | Freund | 435/2 |
| 2009/0310138 A1 | * | 12/2009 | Vanhanen et al. | 356/433 |
| 2010/0021994 A1 | * | 1/2010 | Karasawa | 435/288.7 |
| 2010/0136668 A1 | * | 6/2010 | Hedrick et al. | 435/283.1 |
| 2010/0311150 A1 | * | 12/2010 | Tamura et al. | 435/287.1 |
| 2010/0317099 A1 | * | 12/2010 | Leach et al. | 435/325 |
| 2011/0206646 A1 | * | 8/2011 | Alfonso et al. | 424/93.7 |
| 2011/0299085 A1 | * | 12/2011 | Preiner et al. | 356/436 |

OTHER PUBLICATIONS

Kurita Masakazu et al: Influences of centrifugation on cells and tissues in liposuction aspirates: optimized centrifugation for lipotransfer and cell isolation, Mar. 2008.
Plastic and Reconstructive Surgery Mar. 2008, pp. 1033-1041.
Matsumoto Daisuke et al: "Cell-assisted lipotransfer: supportive use of human adipose-derived cells for soft tissue augmentation with lipoinjection." Nov. 2006.
Tissue Engineering, vol. 12, No. 12, Dec. 2006, pp. 3375-3382.

* cited by examiner

*Primary Examiner* — Gordon Stock, Jr.
(74) *Attorney, Agent, or Firm* — Norton R. Townsley; Belasco Jacobs & Townsley, LLP

(57) ABSTRACT

A method and device for processing mammalian adipose tissue such that the vascular rich fraction is separated from the vascular poor fraction, Mammalian adipose tissue in the form of morselated surgical biopsies and/or lipoaspirate from liposuction is placed within a novel syringe attached to a detection device measuring either color, light saturation, infra-red light, heme, iron or oxygen saturation. This process involves no label and minimal manipulation and handling of the tissue. This process and device may also be used intra-operatively under sterile conditions for immediate use within the same individual receiving liposuction or surgery.

19 Claims, 4 Drawing Sheets

METHOD AND APPARATUS FOR INCREASING ADIPOSE VASCULAR FRACTION

CROSS REFERENCE TO RELATED APPLICATIONS

The inventors claim the benefit of their prior filed Provisional Application Ser. No. 61/136,931, filed Oct. 15, 2008.

BACKGROUND OF THE INVENTION (1) Field of the Invention

The present invention relates to a method and device to separate enriched vascular adipose tissue from mammalian fat. In one example of the application, the tissue may be derived from liposuctioned adipose tissue.

(2) Description of the Related Art

Adipocytes are the cells that primarily compose adipose tissue, specialized in storing energy as fat. There are two types of adipose tissue, white adipose tissue (WAT) and brown adipose tissue (BAT), which are also known as white fat and brown fat, respectively, and comprise two types of fat cells.

In histology, adipose tissue or body fat or just fat is loose connective tissue composed of adipocytes. Adipose tissue is derived from lipoblasts. Its main role is to store energy in the form of fat, although it also cushions and insulates the body. Obesity or being overweight in humans and most animals does not depend on body weight but on the amount of body fat. Adipose tissue also serves as an important endocrine organ by producing hormones such as leptin, resistin, and the cytokine TNFα. The formation of adipose tissue appears to be controlled by the adipose gene. Adipose tissue was first identified by the Swiss naturalist Conrad Gessner in 1551.

Liposuction, also known as lipoplasty ("fat modeling"), liposculpture suction lipectomy or simply lipo ("suction-assisted fat removal") is a cosmetic surgery operation that removes fat from many different sites on the human body. Areas affected can range from the abdomen, thighs, buttocks, to the neck, backs of the arms and elsewhere.

Auto lipo-transfer is removing fat by liposuction processing it and transferring it back into the original host for purposes of primarily aesthetic and cosmetic enhancement, or skin/tissue/wound/scar defect correction or regeneration.

Autologous stem cell transplantation is a procedure in which stem cells are removed, and/or processed, and/or stored, and later given back to the same person.

Growth medium or culture medium is a liquid or gel designed to support the growth of microorganisms or cells, or small plants like the moss Physcomitrella patens. There are different types of media for growing different types of cells.

There are two major types of growth media: those used for cell culture, which use specific cell types derived from plants or animals, and microbiological culture, which are used for growing microorganisms, such as bacteria or yeast. The most common growth media for microorganisms are nutrient broths and agar plates; specialized media are sometimes required for microorganism and cell culture growth. Some organisms, termed fastidious organisms, require specialized environments due to complex nutritional requirements. Viruses, for example, are obligate intracellular parasites and require a growth medium composed of living cells.

Adipose derived stem cells (ADSC) have been found to exhibit pleuripotential and regenerative capabilities with the promise of much therapeutic potential. However, more recent studies suggest that cells removed from contact with their native matrix can exhibit neoplastic behavior or abnormal differentiation. Additionally, isolated ADSC in the animal model clearly demonstrates the loss of cell adhesion and increased metastatic capability despite use of many different matrices to prevent movement of ADSC from the original injection site. A safe alternative to direct removal and isolation of ADSC, therefore, is both necessary and critical.

The anatomic location of ADSC is within the perivascular space of fat. Therefore, fractions of fat rich in microvasculature will have a higher concentration of ADSC. The process of isolating ADSC by direct enzyme degradation or mechanical separation has been proposed by others and presents a labor intensive method of ADSC procurement. An example of isolating ADSC from lipoaspirate fat is illustrated in U.S. Pat. No. 6,777,231. However, this method of separating the ADSC from native matrix and tissue is not only inconvenient, time consuming and expensive, it is also potentially dangerous in that physically detached cells may exhibit tumor like characteristics when heavily manipulated during separation. Moreover the equipment utilized for the method detailed in U.S. Pat. No. 6,777,231 is prohibitively expensive to purchase and maintain. For this reason an alternative method for separating adipose rich fractions of adipose tissue from lipoaspirate without harsh chemical or enzymatic treatment or potentially dangerous cellular labeling is needed.

Development of an alternative method which can separate adipose rich fractions of adipose tissue from lipoaspirate without harsh chemical or enzymatic treatment or potentially dangerous cellular labeling represents a great improvement in the field of liposuction and satisfies a long felt need of the medical profession.

SUMMARY OF THE INVENTION

This invention is a method of increasing the vascular fraction of adipose tissue comprising the steps of:

breaking down adipose tissue into small pieces;

washing the pieces to remove blood, tumescent fluid and detached ADSC;

placing the washed pieces in a container;

processing the container so that oil, vascular rich fat, vascular poor fat and aqueous phases separate into layers; the vascular poor fat having a pure yellow color; the vascular rich fat having an orange color;

attaching the container to a detection chamber in a detection device so that the material within the tube (i.e. all the layers described above) are urged out of the tube in order;

applying pressure to the container;

removing and discarding the aqueous phase;

collecting the vascular rich fat;

detecting with the detection device when the vascular poor fat layer reaches the detection chamber; and ceasing to apply pressure to the container.

Preferably the pieces are small enough to pass through a liposuction cannula. Preferably the container is a syringe. Alternatively the container is a tube with a tapered fitting at its lower end. Preferably the tapered fitting is a Luer-Lok®.

Preferably processing is performed via application of centrifugal force. Pressure can be applied by mechanical means or by pressurized gas.

Finally, the collected vascular rich fat may be transferred into any mammalian host.

The fat can be broken down with any suitable form of energy, including: laser, sonic and radio wavelength. More specifically, the fat can be broken down with any suitable method including: lithotripsy, hyfrecation, phacoemulsification, sonication, rotating blades, serial filtration, and forced screen filtration. Alternately, the fat can be broken down with any suitable chemical means including: collagenase and hypertonic media.

Washing can be accomplished with a material including saline, tissue culture media and phosphate buffered solution. Suitable tissue culture media include: GMEM, RPMI, Eagle's, Fischer's, DMEM, Iscove's, McCoy's, L-15, DME-F1, and Ham's F12 or equivalent. The washing step may further include the use of a filter of pore size that allows single cells of ADSC to pass through.

A non-toxic gradient may be added to the container to improve separation of the layers. The non-toxic gradient may be: tissue culture media (as described above), Histopaque 1077, wax, petroleum jelly, Percoll and CsCl or equivalent.

The detection device may be a spectrophotometer a colorimeter or an oximeter. Thus the detection device can detects when the vascular poor fat layer reaches the detection chamber by color or a selected wavelength of electromagnetic radiation.

This invention is also a device for detecting when a vascular rich fat layer has passed through a container containing a material including the vascular rich fat layer and a vascular poor fat layer comprising:

a means for applying pressure on the material in the container;

a detection chamber for containing material pushed out of the container;

a light source positioned at one side of the detection chamber outputting light of a selected wavelength; the detection chamber being translucent or transparent to the selected wavelength;

light;

a photodetector positioned opposite the detection chamber detecting the control electronics connected to the photodetector; and an indicator connected to the electronics.

The indicator may be a lever, audio alarm, servomechanism (the latter stopping the progress of the material in the container upon detection that the material in the container has absorbed light at a preselected wavelength) or a light.

The selected wavelength may correspond to the pure yellow color of the vascular poor fat (about 570 nm), or the absorption wavelength of iron in hemoglobin, or the pure orange color of the vascular rich fat (about 590 nm) or the absorption wavelength of oxygenated hemoglobin (600 to 750 nm) or the absorption wavelength of deoxygenated hemoglobin (850 to 1000 nm). The light source and the photodetector may be positioned on the same side of the collection tube (reflectance spectroscopy) or on opposite sides of the collection tube (transmission spectroscopy).

The device may be disposable or sterilizable. The container may be a syringe or a container with a tapered fitting (a Luer-Lok®).

The means for applying pressure may be a piston in which case the invention may further comprise:

a motor connected to the control electronics;

a second means for applying pressure activated by the motor and positioned to push on the piston; and the control electronics is additionally programmed to turn off the motor when the material in the detection chamber absorbs at the selected wavelength.

The means for applying pressure may be pressurized gas in which case the invention may further comprise:

a solenoid valve connected to the control electronics and the means for applying pressure; and the control electronics is additionally programmed to activate the solenoid valve when the material in the tube absorbs at the selected wavelength.

An appreciation of the other aims and objectives of the present invention and an understanding of it may be achieved by referring to the accompanying drawings and description of a preferred embodiment.

DETAILED DESCRIPTION OF THE PREFERRED EMBODIMENT

Figure 1:
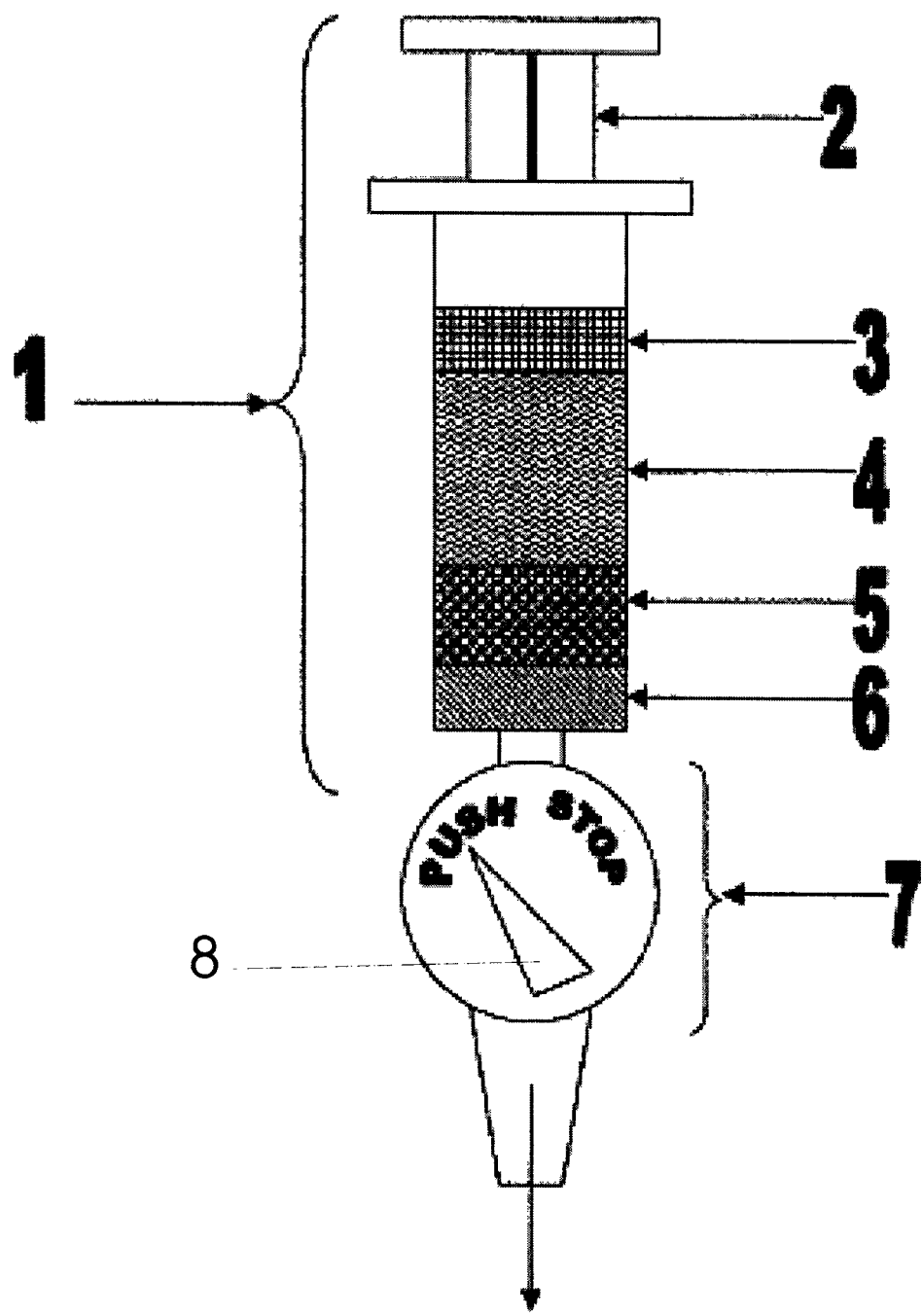
FIG. 1 is a drawing of a preferred embodiment of the invention after the washed adipose tissue has been transferred into a syringe and centrifuged to separate the oil, fat, vascular rich fat and aqueous phase. Connected to the base of the syringe is a color detection device that is able to distinguish pure yellow fat from vascular rich yellow fat. Note that the indicator is in the PUSH position.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

The following glossary should be used when reading this document.

Autograft—a tissue or organ that is grafted into a new position on the body of the individual from which it was removed.

Autolipotransfer: see lipotransfer. Same as lipotransfer but more specifically indicates the fat comes from the same person, hence autologous or "auto" for abbreviation purposes. This is nomenclature is commonly used and defined as above in the field of cosmetic, reconstructive surgery.

Avascular—not associated with or supplied by blood vessels.

Cannula—a metal tube for insertion into the body to draw off fluid or to introduce medication.

Heme—a deep-red iron-containing blood pigment, $C_{34}H_{32}N_4O_4Fe$, obtained from hemoglobin.

Hyfrecation—a method of ablation or cauterization via energy delivery to tissue.

Infranatant—the bottom liquid phase of liposuction fluid within the liposuction container as opposed to the more buoyant, less dense supranatant (upper phase) which usually contains the fat and oil.

Lipoaspirate—the combination of fat, tumescent fluid, blood and serous fluid that is aspirated out in the process of performing liposuction.

Liposuction—the surgical withdrawal of excess fat from local areas under the skin by means of a small incision and vacuum suctioning.

Lipotransfer the process of harvesting fat from one region of the body and transplanting to another region for cosmetic, regenerative or reconstructive surgery purposes.

Lithotripsy—pulverization of kidney stones or gallstones by means of a lithotripter.

Lithotripter—a device used for fragmenting kidney stones with ultrasound waves

Micrograft a smaller graft which can and often is visible only under high powered magnification or biochemical assay or cytometry.

Morselated—cut into smaller pieces.

Morsellized—to have been cut into smaller pieces.

Neoplasm—an abnormal growth of tissue in animals or plants. Neoplasms can be benign or malignant. Also called tumor.

Neoplastic—of or related to or having the properties of a neoplasm.

Perivascular—of, relating to, occurring in, or being the tissues surrounding a blood vessel.

Phacoemulsification—the removal of a cataract by first liquefying the affected lens with ultrasonic vibrations and then extracting it by suction.

Pluripotential—to have the potential of being pluripotent.

Pluripotent—not fixed as to developmental potentialities: having developmental plasticity.

Sonication—the process of dispersing, disrupting, or inactivating biological materials, such as viruses, by use of soundwave energy.

Spectrophotometric—of or pertaining to a spectrophotometer or a spectrograph.

Spectrophotometer—an instrument for making photometric comparisons between parts of spectra.

Tissue culture media—a solution of balanced salts which prevent cells from dehydrating or lysing. They sometimes also contain additional nutrients to ensure long term cell viability.

Xenograft—a graft obtained from a member of one species and transplanted to a member of another species.

Those familiar with the field of aesthetic surgery are aware that adipose tissue may be commonly obtained from liposuction and may be performed wet (with tumescent fluid) or dry (without tumescent). Adipose tissue may also be excised by sharp surgical dissection as well.

In this invention, the procured adipose tissue is then mechanically or chemically disrupted such that the tissue is broken down into small pieces: preferably small enough to traverse easily through a liposuction cannula. Disruption can be done with any suitable form of energy or apparatus such as, but not limited to, laser, lithotripsy, hyfrecation, phacoemulsification, sonication, radio wavelength, rotating blades, serial filtration, and forced screen filtration.

The morsellized adipose tissue is collected into a liposuction canister along with the tumescent fluid, if used, during the surgical procedure. The adipose tissue is then washed with saline or some tissue culture media, such as Iscove's Media (Iscove's Modified Dulbecco's Media are a highly enriched synthetic media well suited for rapidly proliferating, high-density cell cultures), Eagle's Medium (A tissue-culture medium, developed by H. Eagle, containing vitamins, amino acids, inorganic salts and serous enrichments, and dextrose), GMEM, RPMI, Fischer's, DMEM, McCoy's, L-15, DME-F1, or Ham's F12 to remove blood and tumescent fluid. The wash step will also wash away detached ADSC significantly isolated from their native matrix and fatty tissue.

A filter of any suitable pore size that allows passage of single cells the size of ADSC may also be used to further allow washing and purification of the morsellated fatty tissue. The cleansed fat is not exposed to any further enzymatic, chemical, or mechanical breakdown.

The fat is then placed within a container and processed to allow separation of oil, fat and the aqueous phase. The container is preferably a syringe but any container with a bottom connector, such as a test tube with a Luer-Lok ® connector would work. Luer taper is a standardized system of small-scale fluid fittings used for making leak-free connections between a male-taper fitting and its mating female part on medical and laboratory instruments, including hypodermic syringe tips and needles or stopcocks and needles. Processing is preferably in a centrifuge but allowing the fat to settle so that the different components settle into layers by gravity is an alternate. Any number of commercially produced centrifuges can be employed. One that has been found satisfactory is the Hettich model EBA 20 Type 2002-01.

Various non-toxic gradients may also be added to allow further separation of the fatty phase into vascular rich (towards the bottom near the aqueous phase) versus vascular poor (towards the top near the oil fraction). The container is then gently lifted out of the centrifuge and attached to tubing which passes through a colorimetric or spectrophotometric reader. Pressure is applied to the container and the aqueous phase is removed and discarded followed by passage of the vascular rich phase in to a separate collecting syringe or container. Once the pure yellow (vascular poor) adipose layer is detected, the detector indicates to stop and no further pressure is applied to the syringe. The new syringe filled with the vascular rich fraction is ready for immediate lipotransfer into any mammalian host. This vascular rich fraction can be treated with additional medicines or chemotherapeutics prior to injection for the purpose of improving engraftment, augmentation, cell differentiation, wound healing, cosmesis, and aesthetic appearance.

FIG. 1 is a conceptual drawing the invention in an ideal configuration with the washed adipose tissue transferred into a syringe 1 and centrifuged to separate the oil 3, fat 4, vascular rich fat 5 and aqueous phase 6. The aqueous phase 6 results because mammalian tissue contains water, and water may be added during the liposuction procedure and washing steps. Connected to the base of the syringe is a spectrophotometer 7 that is able to distinguish pure yellow fat 4 from vascular rich fat 5. Many suitable spectrophotometers are available. Many spectrophotometers are manufactured by Hach of Loveland, Colo. One suitable instrument is the Hach DR 2700 which may need to be modified to accommodate the tube 11 shown in FIG. 3. The indicator 8 shows that the plunger 2 of the syringe 1 may be pushed.

Figure 2:
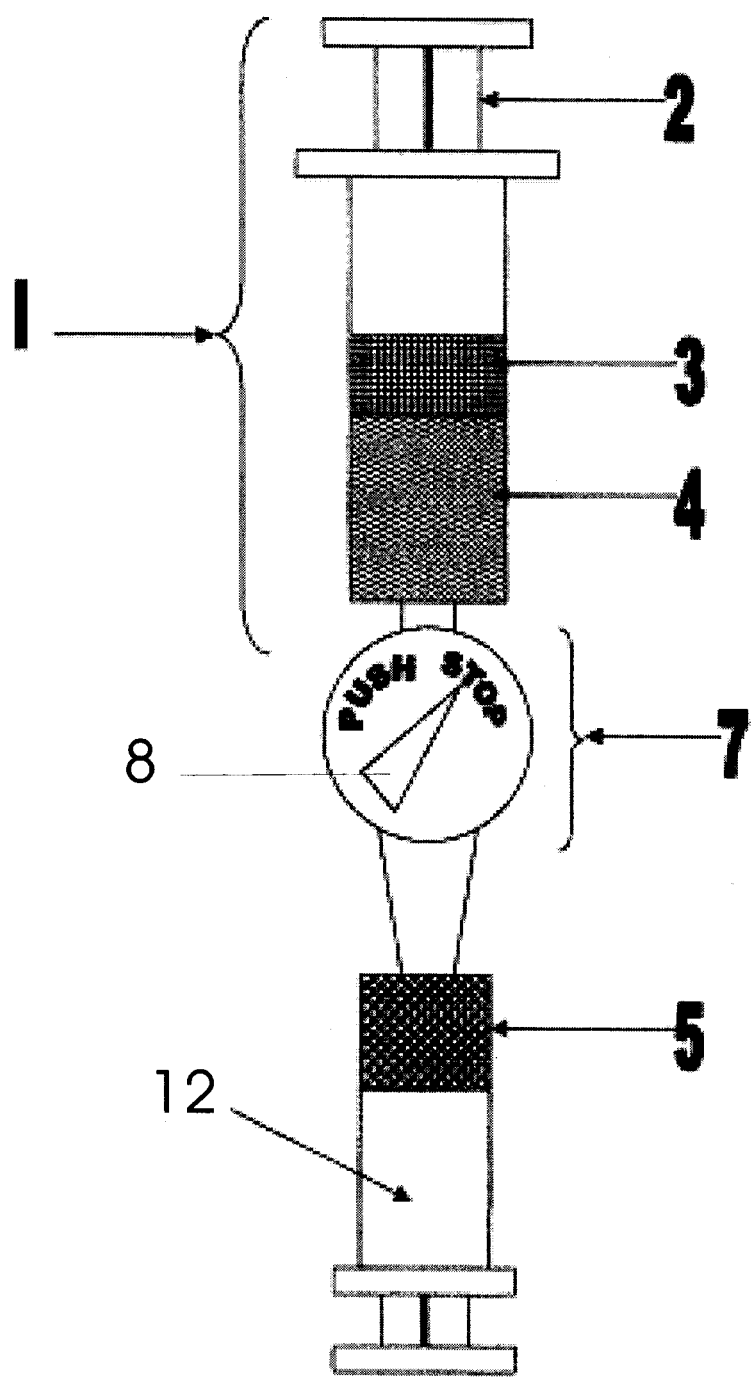
FIG. 2 is a drawing of a preferred embodiment of the invention after the vascular rich fatty layer has been transferred from the top syringe into a new therapeutic syringe below. Note the indicator is now detecting the vascular poor fraction and has switched to the STOP position. The vascular poor fraction and the oil phase are left within the original top syringe.

FIG. 2 is a conceptual drawing of the invention in the final step when the vascular rich fatty layer 5 is transferred from the top syringe 1 into a new therapeutic syringe 12 below. Note the spectrophotometer 7 now detects the vascular poor fraction 4 and the indicator 8 is telling the user not to push the upper syringe piston 2 any further. Vascular poor fat 4 and the oil phase 3 are left within the original top syringe 1 and may be discarded.

Figure 3:
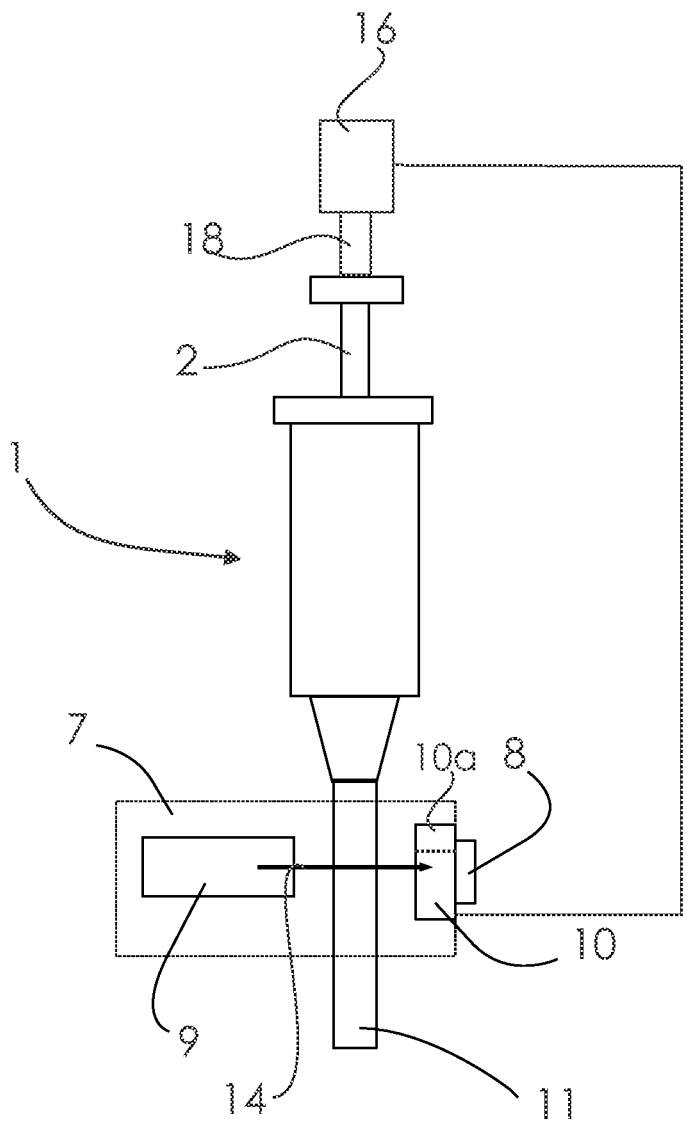
FIG. 3 is a schematic drawing showing in more detail the workings of the detector and a way of automating the preferred embodiment.

FIG. 3 is a schematic drawing showing in more detail the workings of the spectrophotometer 7. The detector 7 includes a light source 9 and a photodetector 10, which includes appropriate control electronics 10a and is connected to the indicator 8. The light source 9 emits light 14 of one or more selected wavelengths and the light 14 passes through the tube 11 containing some of the material pushed out of the syringe 1. The wavelength can be adjusted with a prism or a diffraction grating. Alternatively, LEDs emitting a specific wavelength could be used. The tube, of course, is transparent, or at least translucent, to the selected wavelength.

Figure 4:
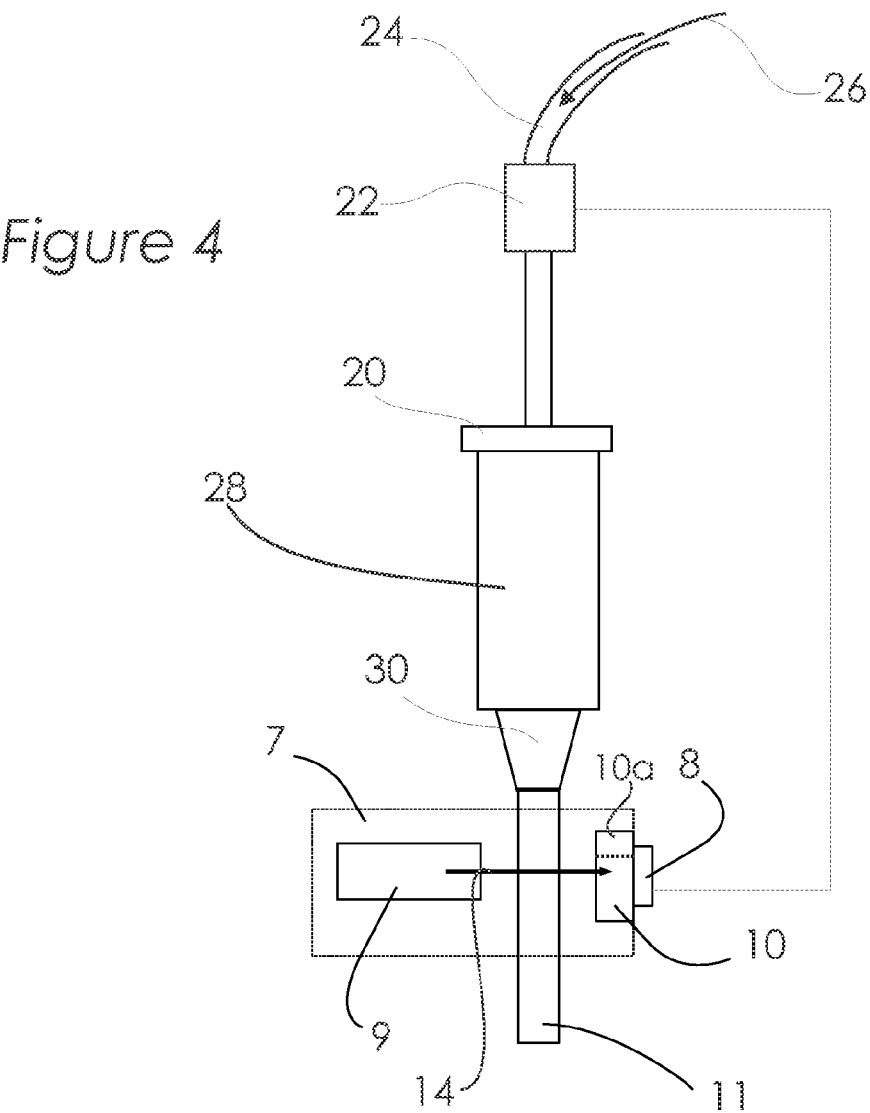
FIG. 4 is a schematic drawing showing an alternate embodiment of this invention and a way of automating this embodiment.

FIG. 4 provides a schematic diagram of an alternate embodiment of this invention. This embodiment includes a test tube or centrifuge tube 28 with a Luer-Lok® fitting 30 at its bottom. Pressure to move the fractions 3, 4, 5, and 6 through the container 28 is provided by compressed gas 26 supplied to the top of the container 28 through a tube 24. The tube 24 is sealed to the top of the container 28 by a seal 20. To turn the supply of compressed gas 26 on and off, a valve 22 is included in the supply line 24.

Since vascular rich fat 5 absorbs at around 590 nm (in the visible range) and the vascular poor fat 4 absorbs at around 570 nm (also in the visible range) the selected wavelength could be either of these.

If a selected wavelength corresponding to vascular poor fat 4 (570 nm) is used, when the material does not absorb light 14 at the selected wavelength, light 14 reaches the photodetector 10, and the electronic control mechanism associated with the photodetector 10 turns the indicator to the PUSH position. When the material absorbs at the selected wavelength, no light 14 reaches the photodetector 10, and the electronic control mechanism associated with the photodetector turns the indicator to the STOP position.

On the other hand if a selected wavelength corresponding to vascular rich fat 5 (590 nm) is used, the material absorbs light 14 at the selected wavelength, light 14 does not reach the photodetector 10, and the electronic control mechanism associated with the photodetector 10 turns the indicator to the PUSH position. When the material starts absorbing at the selected wavelength, light 14 reaches the photodetector 10, and the electronic control mechanism associated with the photodetector turns the indicator to the STOP position.

In fact, to discriminate between vascular poor 4 and vascular rich 5 fat any wavelength in the range from 500 to 700 nm could be used.

The PUSH and STOP positions of the indicator 8 are thus instructions to the operator to push or not push on the piston 2 of the syringe 1. Operation of the syringe 1 in this way could be automated by connecting the photodector 10 electronics to a motor 16 connected to a piston 18 which can push on the piston 2. Then the electronics would be programmed to turn off the motor 16 when the material in the tube 11 absorbs or stops absorbing at the selected wavelength. In other words, the wavelength changes from about 590 nm to about 570 nm or vice versa. Other modifications and enhancements will be obvious to those familiar with the field of spectrophotometry.

In similar fashion, the alternate embodiment of FIG. 4 could be automated by using a solenoid valve 22 and connecting the photodector 10 to this valve 22.

Figure 5:
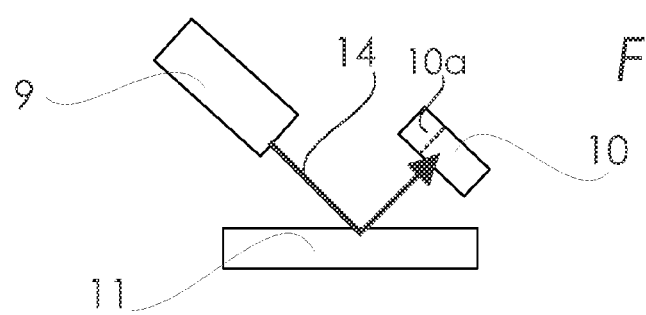
FIG. 5 is a sketch illustrating reflectance spectrophotometry.

The preferred method of detecting is transmission. In the transmission method the light source 9 and photodetector 10 are on opposite sides of the tube 11. In the reflectance method, the light source 9 and photodetector 10 are on the same side of the tube. The light 14 penetrates a short way into the tube 11 and the material therein and bounces from the light source to the photodetector. This is illustrated in FIG. 5. The transmission method, illustrated in FIGS. 3 and 4, is the most common type used.

Clearly indicator lights could be used in place of the indicator 8. In addition, other frequencies could be selected to detect presence or absence of other components in the vascular poor 4 and vascular rich 5 fractions. One component capable of easy detection is hemoglobin (oxygenated, deoxygenated or both). The technique of detecting hemoglobin is called oximetry. Another good component to detect would be iron. Moreover, while a tube 11 is the preferred device for transporting the material in the syringe 1 between the light source 9 and the detector 10, any detection chamber which permits passage of the material could alternatively be used. If tubing 11 alone is used, the "detection chamber" is that portion of the tube 11 where the light 14 passes through.

The principle of oximetry is based on the fact that oxygenated hemoglobin absorbs more infrared light and allows more red light to pass through while deoxygenated hemoglobin absorbs more red light and allows more infrared light to pass through. Red light is in the 600-750 nm wavelength light band. Infrared light is in the 850-1000 nm wavelength light band.

Pulse oximetry uses a light emitter with red and infrared LEDs that shines through a reasonably translucent site with good blood flow. Typical sites are the finger, toe, pinna (top) or lobe of the ear. Opposite the emitter is a photodetector that receives the light that passes through the measuring site.

There are two methods of sending light through the measuring site: transmission and reflectance. In the transmission method the emitter and photodetector are opposite of each other with the measuring site in-between. The light can then pass through the site. In the reflectance method, the emitter and photodetector are next to each other on top of the measuring site. The light bounces from the emitter to the detector across the site. The transmission method is the most common type used and for this discussion the transmission method will be implied.

After the transmitted red (R) and infrared (IR) signals pass through the measuring site and are received at the photodetector, the R/IR ratio is calculated. The R/IR is compared to a "look-up" table (made up of empirical formulas) that converts the ratio to an oxygen saturation ($SpO_2$) value. Most manufacturers have their own look-up tables based on calibration curves derived from healthy subjects at various $SpO_2$ levels. Typically an R/IR ratio of 0.5 equates to approximately 100% $SpO_2$, a ratio of 1.0 to approximately 82% $SpO_2$, while a ratio of 2.0 equates to 0% $SpO_2$.

At the measuring site there are constant light absorbers. They are skin, tissue, venous blood, and the arterial blood. However, with each heart beat the heart contracts and there is a surge of arterial blood, which momentarily increases arterial blood volume across the measuring site. This results in more light absorption during the surge. If light signals received at the photodetector are looked at 'as a waveform', there should be peaks with each heartbeat and troughs between heartbeats. If the light absorption at the trough (which should include all the constant absorbers) is subtracted from the light absorption at the peak then the resultants are the absorption characteristics due to added volume of blood only; which is arterial. Since peaks occur with each heartbeat or pulse, the term "pulse oximetry" was coined.

Proof of the concept of the instant invention was obtained by separating oil, fat and vascular rich fat into separate flasks and photographing each fraction at 4× magnification. The photographs were analyzed for color, hue and saturation to determine if any definable difference could be determined. There was an obvious difference in color, hue and saturation between each layer.

A Datascope pulse oximeter, model: Accustat, part #0998-00-0057-01 was modified and used to determine hemoglobin in each fraction. The gain of the internal toggle switch was turned from ¼ twist to maximum. The computer was "tricked" into reading for $O_2$ saturation by leaving intermittent bubbles of $O_2$ every ½ cc thus simulating pulsatile activity. In this way the specimen could be aspirated back and forth along the IV line which was compressed directly against the LEDs removed from the plastic housing to form a better optical connection. Oil registered 0 max, plain fat registered 0 max, vascular rich fat registered 2-4 max. This was repeated in four independent experiments with three different specimens of fat.

Example of clinical device use:

A 220 lb white female underwent abdominal liposuction for aesthetic reasons. A total of 300 cc of lipoaspirate was obtained. A total of 50 cc of fat was removed from the suction canister and washed three times with 50 cc of phosphate buffered solution (PBS) to remove residual blood and infranatant. Fifty cc of the fat was then further morselated into smaller micrografts using sterile surgical scissors. The fat was filtered using a metal strainer with 1 mm pore size to remove single cells. It was then placed within five 10 cc syringes and centrifuged at 300 g for 15 minutes. Three phases were then appreciated: oil, fat, vascular rich fat, and aqueous. The aqueous phase was easily removed by applying pressure to the syringe but pressure was stopped when the aqueous-vascular rich fat interface was reached. Then the syringe was connected to a second syringe through a tube passing through a colorimetric meter. The meter was turned on and the vascular rich fat fraction was transferred to the second syringe by again pressing on the piston of the first syringe. The piston was advanced until the detector was only able to detect pure yellow vascular poor fat. The vascular rich fat in the second syringe was used for lipotransfer therapy.

This invention is a method for isolating the vascular rich fraction of mammalian adipose tissue for medical therapy. The vascular fraction may be used for soft tissue augmentation of mammalian skin by autolipotransfer or for wound healing by injecting within, beneath and/or around the wound to accelerate wound healing. It may also be used for tissue regeneration by injecting within, beneath and/or around the damaged tissue to accelerate regeneration. Additional specialty tissue culture media and/or gradients may be added to the adipose tissue to allow greater separation of the vascular rich and vascular poor fractions. Additional specialty tissue culture media may be added to the adipose tissue in order to induce differentiation of adipose derived stem cells into ectoderm and/or mesoderm and/or endoderm type tissue. The processed tissue may be used as an allograft, autograft or xenograft.

This invention is also a device composed of a syringe and a detector capable of discriminating solely or in combination any of the following: color, light saturation, infra-red, heme, oxygen and iron to allow discrimination between the yellow avascular fatty fraction, with a color of wavelength about 570 nm, from the orange tinted oxygen and heme rich vascular fat fraction, with a color of wavelength about 590 nm. The detector may be disposable or sterilizable and reusable.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A device that when a vascular rich fat layer has passed through a container containing a material including said vascular rich fat layer and a vascular poor fat layer comprising:
   a) a means for applying pressure on said material in said container;
   b) a detection chamber that contains said material urged out of said container;
   c) a light source positioned at one side of said detection chamber outputting light of a selected wavelength; said detection chamber being translucent or transparent to said selected wavelength;
   d) a photodetector positioned which detects said light;
   e) control electronics connected to said photodetector; and an indicator connected to said electronics;
   said vascular rich fat having a pure orange color, absorbing light at 590 nm and containing oxygenated hemoglobin, which absorbs more infrared light than red light, and deoxygenated hemoglobin, which absorbs more red light than infrared light;
   said vascular poor fat having a pure yellow color and absorbing light at 570 nm.

2. A device as claimed in claim 1 in which said indicator is a lever.

3. A device as claimed in claim 1 in which said indicator is a light.

4. A device as claimed in claim 1 in which said selected wavelength corresponds to the pure yellow color of said vascular poor fat.

5. A device as claimed in claim 1 in which said selected wavelength corresponds to an absorption wavelength of iron in hemoglobin.

6. A device as claimed in claim 1 in which said selected wavelength corresponds to the pure orange color of said vascular rich fat.

7. A device as claimed in claim in which said selected wavelength is in a range of 500 to 700 nm.

8. A device as claimed in claim 1 in which said selected wavelength corresponds to an absorption wavelength of oxygenated hemoglobin, 9. A device as claimed in claim 1 in which said selected wavelength is in a range of 600 to 750 nm.

10. A device as claimed in claim 1 in which said selected wavelength corresponds to an absorption wavelength of deoxygenated hemoglobin, 11. A device as claimed in claim 1 in which said selected wavelength is in a range of 850 to 1000 nm.

12. A device as claimed in claim 1 in which said light source and said photodetector are positioned on a same side of said detection chamber.

13. A device as claimed in claim 1 in which said light source and said photodetector are positioned on opposite sides of said detection chamber.

14. A device as claimed in claim 1 in which said device is sterilizable.

15. A device as claimed in claim 1 in which said container is a syringe.

16. A device as claimed in claim 1 in which said means for applying pressure is a piston.

17. A device as claimed in claim 16 further comprising:
   a) a motor connected to said control electronics positioned to push on said piston;
   b) said control electronics is additionally programmed to turn off said motor when said material in said detection chamber absorbs at said selected wavelength.

18. A device as claimed in claim 1 in which said means for applying pressure is pressurized gas.

19. A device as claimed in claim 18 further comprising:
   a) a solenoid valve connected to said control electronics and said means for applying pressure; said control electronics is additionally programmed to activate said solenoid valve when said material in said detection chamber absorbs at said selected wavelength.

\* \* \* \* \*